United States Patent [19]

Roling et al.

[11] Patent Number: 4,883,580
[45] Date of Patent: Nov. 28, 1989

[54] METHODS FOR DEACTIVATING IRON IN HYDROCARBON FLUIDS

[75] Inventors: Paul V. Roling, Spring, Tex.; Joseph H. Y. Niu, Wanaque, N.J.

[73] Assignee: Betz Laboratories, Inc., Trevose, Pa.

[21] Appl. No.: 338,018

[22] Filed: Apr. 14, 1989

Related U.S. Application Data

[62] Division of Ser. No. 201,655, Jun. 1, 1988, Pat. No. 4,847,415.

[51] Int. Cl.$^4$ .............................................. C10G 29/20
[52] U.S. Cl. .................................. 208/48 AA; 208/177; 208/290; 208/291; 585/864
[58] Field of Search .................... 208/48 AA, 177, 290, 208/291; 585/864

[56] References Cited

U.S. PATENT DOCUMENTS

| | | | |
|---|---|---|---|
| Re. 26,330 | 1/1968 | Colfer | 208/48 |
| 2,347,626 | 4/1944 | Bradley | 106/273 |
| 2,353,192 | 7/1944 | Sargent et al. | 44/62 |
| 2,553,441 | 5/1951 | Chenicek | 99/163 |
| 2,962,442 | 11/1960 | Andress | 252/51.5 |
| 3,023,161 | 2/1962 | Luvisi et al. | 208/251 |
| 3,034,876 | 5/1962 | Gee et al. | 44/62 |
| 3,050,461 | 8/1962 | Luvisi | 208/251 |
| 3,068,083 | 12/1962 | Gee et al. | 44/70 |
| 3,132,085 | 5/1964 | Summers, Jr. | 208/48 |
| 3,200,106 | 8/1965 | Dickson et al. | 260/97.5 |
| 3,214,376 | 10/1965 | Morway | 252/18 |
| 3,225,099 | 12/1965 | Coffield | 260/570.9 |
| 3,235,484 | 2/1966 | Colfer | 208/48 |
| 3,269,810 | 8/1966 | Chamot | 44/62 |
| 3,355,270 | 11/1967 | Amick et al. | 44/68 |
| 3,413,347 | 11/1968 | Werrel | 260/570.5 |
| 3,437,583 | 4/1969 | Gonzalez | 208/48 |
| 3,442,791 | 5/1969 | Gonzalez | 208/48 |
| 3,756,943 | 9/1973 | Hopkins et al. | 208/143 |
| 3,787,458 | 1/1974 | Piasek et al. | 260/404.5 |
| 3,980,569 | 9/1976 | Pindar et al. | 252/51.5 R |
| 3,985,802 | 10/1976 | Piasek et al. | 260/553 A |
| 4,020,048 | 4/1977 | Harrop | 260/51.5 |
| 4,032,304 | 6/1977 | Dorer, Jr. | 44/70 |
| 4,157,308 | 6/1979 | Wilgus et al. | 252/42.7 |
| 4,157,309 | 6/1979 | Wilgus et al. | 252/42.7 |
| 4,166,726 | 9/1979 | Harle | 44/73 |
| 4,170,562 | 10/1979 | West | 252/51.5 A |
| 4,242,212 | 12/1980 | Hanson | 252/51.5 R |
| 4,396,517 | 8/1983 | Gemmill, Jr. et al. | 252/51.5 R |
| 4,491,654 | 1/1985 | Cummings | 564/367 |
| 4,539,099 | 9/1985 | Merchant et al. | 208/177 |
| 4,548,725 | 10/1985 | Bridger | 252/56 R |
| 4,666,683 | 5/1987 | Brown et al. | 423/DIG. 14 |
| 4,714,750 | 12/1987 | Grigsby et al. | 564/367 |
| 4,749,468 | 6/1988 | Roling et al. | 208/48 AA |
| 4,775,459 | 10/1988 | Forester | 208/48 AA |
| 4,810,354 | 3/1989 | Roling et al. | 208/48 AA |
| 4,847,415 | 7/1989 | Roling et al. | 564/367 |

FOREIGN PATENT DOCUMENTS 1158076   7/1969   United Kingdom ................ 564/367

OTHER PUBLICATIONS

Pedersen, C. J., "Inhibition of Deterioration of Cracked Gasoline During Storage", *Industrial and Engineering Chemistry* 41:924–928 (May 1949).

*Primary Examiner*—Anthony McFarlane
*Attorney, Agent, or Firm*—Alexander D. Ricci; Roslyn T. Tobe

[57] ABSTRACT

Certain Mannich reaction products (i.e., alkylated phenol, polyoxyalkylenediamine, and an aldehyde) are used to deactivate iron species already present in hydrocarbon fluids. Left untreated, such iron species lead to decomposition resulting in the formation of gummy, polymer masses in the hydrocarbon liquid.

9 Claims, No Drawings

METHODS FOR DEACTIVATING IRON IN HYDROCARBON FLUIDS

This is a divisional of application Ser. No. 201,655, filed June 1, 1988, now U.S. Pat. No. 4,847,415.

BACKGROUND OF THE INVENTION

This invention relates to the use of chelating molecules to deactivate iron species to prevent fouling in hydrocarbon fluids.

In a hydrocarbon stream, saturated and unsaturated organic molecules, oxygen, peroxides, and metal compounds are found, albeit the latter three in trace quantities. Of these materials, peroxides can be the most unstable, decomposing at temperatures from below room temperature and above depending on the molecular structure of the peroxide (G. Scott, "Atmospheric Oxidation and Antioxidants", published by Elsevier Publishing Co., NY, 1965).

Decomposition of peroxide will lead to free radicals, which then can start a chain reaction resulting in polymerization of unsaturated organic molecules. Antioxidants can terminate free radicals that are already formed.

Metal compounds and, in particular, transition metal compounds such as copper and iron can initiate free radical formation in three ways. First, they can lower the energy of activation required to decompose peroxides, thus leading to a more favorable path for free radical formation. Second, metal species can complex oxygen and catalyze the formation of peroxides. Last, metal compounds can react directly with organic molecules to yield free radicals.

The first row transition metal species manganese, iron, cobalt, nickel, and copper are already found in trace quantities (0.01 to 100 ppm) in crude oils, in hydrocarbon streams that are being refined, and in refined products. C. J. Pedersen (Ind. Eng. Chem., 41, 924–928, 1949) shows that these transition metal species reduce the induction time for gasoline, an indication of free radical initiation. Copper compounds are more likely to initiate free radicals than the other first row transition elements under these conditions.

To counteract the free radical initiating tendencies of the transition metal species so called metal deactivators are added to hydrocarbons with transition metal species already in the hydrocarbon. These materials are organic chelators that tie up the orbitals on the metal rendering the metal inactive. When metal species are deactivated, fewer free radicals are initated and smaller amounts of antioxidants would be needed to inhibit polymerization.

Not all chelators will function as metal deactivators. In fact, some chelators will act as metal activators. Pedersen showed that while copper is deactivated by many chelators, other transition metals are only deactivated by selected chelators.

PRIOR ART

Schiff Bases such as N,N'-salicylidene-1,2-diaminopropane are the most commonly used metal deactivators. In U.S. Pat. Nos. 3,034,876 and 3,068,083, the use of this Schiff Base with esters were claimed as synergistic blends for the thermal stabilization of jet fuels.

Gonzalez, in U.S. Pat. No. 3,437,583 and 3,442,791, claimed the use of N,N'-disalicylidene-1,2-diaminopropane in combination with the product from the reaction of a phenol, an amine, and an aldehyde as a synergistic antifoulant. Alone the product of reaction of the phenol, amine, and aldehyde had little, if any, antifoulant activity.

Products from the reaction of a phenol, an amine, and an aldehyde (known as Mannich-type products) have been prepared in many ways with differing results due to the method of preparation and due to the exact ratio of reactants and the structure of the reactants.

Metal chelators were prepared by a Mannich reaction in U.S. Pat. No. 3,355,270. Such chelators were reacted with copper to form a metal chelate complex. The metallic complex was then added to the furnace oil as a catalyst to enhance combustion.

Mannich-type products were used as dispersants in U.S. Pat. Nos. 3,235,484 and Re. 26,330 and 4,032,304 and 4,200,545. A Mannich-type product in combination with a polyalkylene amine was used to provide stability in preventing thermal degradation of fuels in U.S. Pat. No. 4,166,726.

Copper, but not iron, is effectively deactivated by metal chelators such as N,N'-disalicylidene-1,2-diaminopropane. Mannich-type products, while acting as chelators for the preparation of catalysts or as dispersants, have not been shown to be transition metal ion deactivators.

DESCRIPTION OF THE INVENTION

Accordingly, it is an object of the inventors to provide an effective iron deactivator for use in hydrocarbon mediums so as to inhibit free radical formation during the high temperature (e.g., 100°–1000° F., commonly 600°–1000° F.) processing of the hydrocarbon fluid. It is an even more specific object to provide an effective iron deactivator that is capable of performing efficiently even when used at low dosages.

We have found that iron is effectively deactivated by the use of certain Mannich-type products formed via reaction of the reactants (A), (B), and (C); wherein (A) is an alkyl substituted phenol of the structure.

FORMULA (I)

wherein R is selected from alkyl, aryl, alkaryl, or arylalkyl of from about 1 to 20 carbon atoms; wherein (B) is a polyoxyalkylenediamine selected from the group consisting of

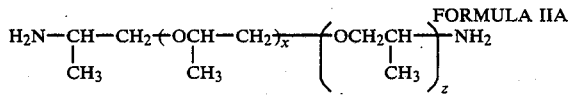

FORMULA IIA where the sum of x and z is from 1 to 6 and

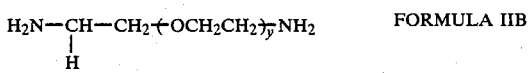

FORMULA IIB where y is from 1 to 6; and wherein (C) is an aldehyde of the structure

FORMULA (III)

wherein $R_1$ is selected from hydrogen and an alkyl having from 1 to 6 carbon atoms.

As to exemplary compounds falling within the scope of Formula I supra, p-cresol, 4-ethylphenol, 4-t-butylphenol, 4-t-amylphenol, 4-t-octylphenol, 4-dodecylphenol, and 4-nonylphenol may be menioned. At present, it is preferred to use 4-nonylphenol as the Formula I component.

Exemplary polyoxyalkylenediamines which can be used in accordance with Formula II include dipropylene glycol diamine, tripropylene glycol diamine, tetrapropylene glycol diamine, diethylene glycol diamine, triethylene glycol diamine, tetraethylene glycol diamine and mixtures thereof.

The aldehyde component can comprise, for example, formaldehyde, acetaldehyde, propanaldehyde, butrylaldehyde, hexaldehyde, heptaldehyde, etc. with the most preferred being formaldehyde which may be used in its monomeric form, or, more conveniently, in its polymeric form (i.e., paraformaldehyde).

As is conventional in the art, the condensation reaction may proceed at temperatures from about 50° to 200° C. with a preferred temperature range being about 75°–175° C. As is stated in U.S. Pat. No. 4,166,726, the time required for completion of the reaction usually varies from about 1–8 hours, varying of course with the specific reactants chosen and the reaction temperature.

As to the molar range of components (A):(B):(C) which may be used, this may fall within 0.5–5:1:0.5–5.

The iron deactivator of the invention may be dispersed within the hydrocarbon medium within the range of about 0.05 to 50,000 ppm based upon one million parts of the hydrocarbon medium. Preferably, the iron deactivator is added in an amount from about 1 to 10,000 ppm. A Mannich product-metal complex is formed in situ upon Mannich product addition to the hydrocarbon medium. The complex deactivates the metal so as to inhibit free radical formation.

EXAMPLES

The invention will now be further described with reference to a number of specific examples which are to be regarded solely as illustrative and not as restricting the scope of the invention.

Testing Method

The peroxide test was employed to determine the deactivating ability of the chelators. The peroxide test involves the reaction of a metal compound, hydrogen peroxide, a base, and a metal chelator. In the presence of a base, the metal species will react with the hydrogen peroxide yielding oxygen. When a metal chelator is added, the metal can be tied up resulting in the inhibition of the peroxide decomposition or the metal can be activated resulting in the acceleration of the rate of decomposition. The less oxygen generated in a given amount of time, the better the metal deactivator.

A typical peroxide test is carried out as follows: In a 250 mL two-necked, round-bottomed flask equipped with an equilibrating dropping funnel, a gas outlet tube, and a magnetic stirrer, was placed 10 mL of 3% (0.001 mol) hydrogen peroxide in water, 10 mL of a 0.01M (0.0001 mol) metal naphthenate in xylene solution, and metal deactvator. To the gas outlet tube was attached a water-filled trap. The stirrer was started and stirring kept at a constant rate to give good mixing of the water and organic phases. Ammonium hydroxide (25 mL of a 6% aqueous solution) was placed in the dropping funnel, the system was closed, and the ammonium hydroxide added to the flask. As oxygen was evolved, water was displaced, with the amount being recorded as a factor of time. A maximum oxygen evolution was 105 mL. With metal species absent, oxygen was not evolved over 10 minutes.

Example 1

A 2:1:2 mole ratio of 4-nonylphenol:triethylene glycol diamine:paraformaldehyde was prepared as follows. In a three-necked, round-bottomed flask equipped with a mechanical stirrer, a reflux condenser, and a thermometer was placed 55 g (0.25 mole) of nonylphenol, 7.88 g (0.25 mole) of paraformaldehyde, and 76.9 g of xylene. On addition of the 18.5 g (0.125 mole) of triethylene glycol diamine, the temperature rose to 63° C. The mixture was held at about 70° C. for 1 hour wherein a reaction product was formed. A Dean Stark trap was inserted between the condenser and the flask and the temperature was increased to 150° C., by which time water of formation was azeotroped off—4.5 mL was collected (approximately the theoretical amount). The reaction product was cooled to room temperature, the xylene was condensed and was returned to the reaction product to form a mixture, and the mixture was used at a concentration of 50% reaction product.

When 100 mg of the reaction product in the above mixture was used in the peroxide test, only 37 mL of oxygen was evolved in 5 minutes. In contrast, when the product was not used in the peroxide test, 72 mL of oxygen was evolved.

This example shows that the product reduced the iron activity by 49%.

Example 2

A 2:1:2 mole ratio of p-cresol:triethylene glycol diamine:paraformaldehyde was prepared as follows. In a three-necked, round-bottomed flask equipped with a mechanical stirrer, a reflux condenser, and a thermometer was placed 43.26 g (0.4 mole) of p-cresol, 12.61 (0.4 mole) of paraformaldehyde, and 78.4 g of xylene. On addition of the 29.6 g (0.2 mole) of triethylene glycol diamine, the temperature rose to 66° C. The mixture was held at 70° C. for 1 hour wherein a reaction product was formed. A Dean Stark trap was inserted between the condenser and the flask and the temperature was increased to 150° C., by which time water of formation was azeotroped off—7.4 mL was collected (approximately the theoretical amount). The reaction product was cooled to room temperature, the xylene was condensed and was returned to the reaction product to form a mixture, and the mixture was used at a concentration of 50% reaction product. When 100 mg of the reaction product in the above mixture was used in the peroxide test, 39 mL of oxygen was evolved in 5 minutes. In contrast, when the product was not used in the peroxide test, 72 mL of oxygen was evolved.

This example shows that the product reduced the iron activity by 46%.

Example 3

A 2:1:2 mole ratio of 4-nonylphenol:mixture of tripropylene glycol diamine and tetrapropylene glycol diamine:paraformaldehyde was prepared as follows. In a three-necked, round-bottomed flask equipped with a metchanical stirrer, a reflux condenser, and a thermometer was placed 44 g (0.2 mole) of 4-nonylphenol, 6.30 g (0.2 mole) of paraformaldehyde, and 23.5 g of xylene. On addition of the 23 g (0.1 mole) of the mixture of tripropylene glycol diamine and tetrapropylene glycol diamine, the temperature rose to 63° C. The mixture was held at 70° C. for 1 hour wherein a reaction product was formed. A Dean Stark trap was inserted between the condenser and the flask and the temperature was increased to 151° C., by which time water of formation was azeotroped off—3.6 mL (approximately the theoretical amount). The reaction product was cooled to room temperature, the xylene was condensed was and returned to the reaction product to form a mixture, and the mixture was used at a concentration of 75% reaction product.

When 100 mg of the reaction product in the above mixture was used in the peroxide test, 24 mL of oxygen was evolved in 5 minutes. In contrast, when the product was not used in the peroxide test, 52 mL of oxygen was evolved.

This example shows that the product reduced the iron activity by 54%.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

We claim:

1. A method of deactivating an iron species disposed in a hydrocarbon medium, wherein in the absence of said deactivating said metal would initiate decomposition of the hydrocarbon medium, said method comprising adding to said hydrocarbon medium an effective amount of a Mannich reaction product formed by reaction of reactants (A), (B), and (C); wherein (A) comprises an alkyl substituted phenol of the structure

FORMULA I wherein R is selected from the alkyl, aryl, alkaryl, or arylalkyl of from about 1 to 20 carbon atoms; (B) comprises a polyoxyalkylenediamine selected from the group consisting of

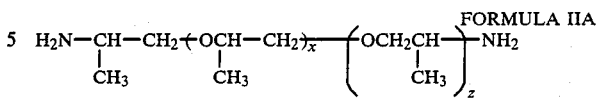

FORMULA IIA where the sum of x and z is from 1 to 6 and

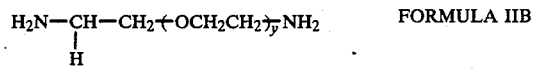

FORMULA IIB where y is from 1 to 6; and (C) comprises an aldehyde of the structure

FORMULA III wherein $R_1$ is selected from H and an alkyl group having from about 1-6 carbon atoms wherein said iron species are deactivated.

2. A method as recited in claim 1, the molar ratio of reactants (A):(B):(C) being within the range of from 0.5–5:1:0.5–5.

3. A method as recited in claim 2 wherein said Mannich reaction product is admitted to said hydrocarbon medium in an amount of from 0.5–50,000 ppm based upon one million parts of said hydrocarbon medium.

4. A method as recited in claim 3 wherein said Mannich reaction product is admitted to said hydrocarbon medium in an amount of 1 to 10,000 ppm based upon one million parts of said hydrocarbon medium.

5. A method as recited in claim 4 wherein said hydrocarbon medium is heated at a temperature of from 100°–1000° F.

6. A method as recited in claim 5 wherein said hydrocarbon medium is heated at a temperature of about 600°–1000° F.

7. A method as recited in claim 5 wherein (A) comprises a member or members selected from the group consisting of p-cresol, 4-ethylphenol, 4-t-butylphenol, 4-t-amylphenol, 4-t-octylphenol, 4-dodecylphenol, and 4-nonylphenol.

8. A method as recited in claim 5 wherein said polyamine (B) is selected from the group consisting of tripropylene glycol diamine and tetrapropylene glycol diamine, triethylene glycol diamine and mixtures thereof.

9. A method as recited in claim 5 wherein said aldehyde (C) is selected from the group consisting of formaldehyde and paraformaldehyde.

* * * * *